United States Patent [19]
Khan et al.

[11] Patent Number: 6,162,433
[45] Date of Patent: Dec. 19, 2000

[54] NON ANTIBIOTIC SELECTABLE MARKERS FOR LIVE VACCINES

[75] Inventors: Mohammed Anjam Khan; Hesta Varey McNeill; Carlos Estenio Hormaeche, all of Newcastle upon Tyne, United Kingdom

[73] Assignee: Medeva Europe Limited, London, United Kingdom

[21] Appl. No.: 09/175,837

[22] Filed: Oct. 19, 1998

Related U.S. Application Data

[63] Continuation of application No. PCT/GB97/01080, Apr. 18, 1997, abandoned.

[30] Foreign Application Priority Data

Apr. 19, 1996 [GB] United Kingdom .................... 9608106

[51] Int. Cl.$^7$ .......................... A61K 39/02; A61K 39/08; A61K 39/108; A61K 39/112; C12N 1/20

[52] U.S. Cl. ..................................... 424/184.1; 424/190.1; 424/200.1; 424/201.1; 424/203.1; 424/204.1; 424/246.1; 424/254.1; 424/257.1; 424/258.1; 424/261.1; 424/264.1; 424/265.1; 424/269.1; 424/270.1; 424/272.1; 435/69.3; 435/91.4; 435/252.3; 435/252.33; 435/320.1

[58] Field of Search .............................. 424/184.1, 190.1, 424/200.1, 201.1, 203.1, 204.1, 246.1, 254.1, 257.1, 258.1, 261.1, 264.1, 265.1, 269.1, 270.1, 272.1; 435/69.3, 91.4, 468, 419, 320.1, 252.3, 252.33

[56] References Cited

PUBLICATIONS

Chabalgoity et al., "A *Salmonella typhimurium htrA* Live Vaccine Expressing Multiple Copies of a Peptide Comprising Amino Acids 8–23 of Herpes Simplex Virus Glycoprotein D as a Genetic Fusion to Tetanus Toxin Fragment C Protects Mice from Herpes Simplex Virus Infection," *Molecular Microbiology*, 19(4):791–801 (1996).

Chatfield et al., "Live Salomella as Vaccines and Carriers of Foreign Antigenic Determinants," *Vaccine*, 7:495–498 (Dec. 1989).

Chatfield et al, "Use of the *nirB* Promoter to Direct the Stable Expression of Heterologous Antigens in *Salmonella* Oral Vaccine Strains: Development of a Single–Dose Oral Tetanus Vaccine," *Bio/Technology*, 10:888–892 (Aug. 1992).

D'Halluin et al., "The *bar* Gene as Selectable and Screenable Marker in Plant Engineering," *Methods in Enzymology*, 216:415–426 (1992).

Edwards et al., "Construction of ΔaroA his Δpur Strains of *Salmonella typhi*," *Journal of Bacteriology*, 170(9):3991–3995 (Sep 1988).

Gonzalez et al., "*Salmonella typhi* Vaccine Strain CVD 908 Expressing the Circumsporozoite Protein of *Plasmodium falciparum*: Strain Construction and Safety and Immunogenicity in Humans," *Journal of Infectious Diseases*, 169:927–931 (1994).

Khan et al., "Construction, Expression, and Immunogenicity of the *Schistosoma mansoni* P28 Glutathione S–transferase as a Genetic Fusion to Tetanus Toxin Fragment C in a Live Aro Attenuated Vaccine Strain of *Salmonella*"*Proc. Natl. Acad. Sci. USA*, 91:11261–11265 (Nov. 1994).

Murakami et al., "The Bialaphos Biosynthetic Genes of *Streptomyces hygroscopicus*: Molecular Cloning and Characterization of the Gene Cluster," *Molecular and General Genetics*, 205:42–50 (1986).

Saiki et al., "Primer–Directed Enzymatic Amplification of DNA with a Thermostable DNA Polymerase," *Science*, 239:487–491 (Jan. 1988).

Thompson et al., "Characterization of the Herbicide–resistance Gene *bar* from *Streptomyces hygroscopicus*," *EMBO Journal*, 6(9):2519–2523 (1987).

Tabor's CYclopedic Medical Dictionary. FA Davis Company, Philadelphia, p. A–140, 1984.

Somers, DA, et al. Fertile, transgenic oat plants. Biotechnology 10:1589–1594, 1992.

Fromm, M.E. Inheritance and expression of chiumeric genes in the progeny of transgenic maize plants. Biotechnology 8:833–839, 1990.

Olive, M, Ret al., The anaerobic responsive element contains two GC–rich sequences essential for binding a nuclear protein and hypoxic activation of the maize Adh1 promoter. Nucl. Acids Res. 19(25):7053–7060, 1991.

*Primary Examiner*—David Saunders
*Assistant Examiner*—Mary B. Tung
*Attorney, Agent, or Firm*—Popovich & Wiles, P.A.

[57] ABSTRACT

The invention relates to DNA constructs encoding a safe, selectable marker, other than an antibiotic resistance marker, vectors and/or cells including said constructs; and vaccines based on said constructs for use in animals and particularly humans. The safe, selectable marker being a marker that confers resistance to an agent, other than an antibiotic, which would otherwise deleteriously affect the growth of a cell in which said construct was placed.

22 Claims, 1 Drawing Sheet

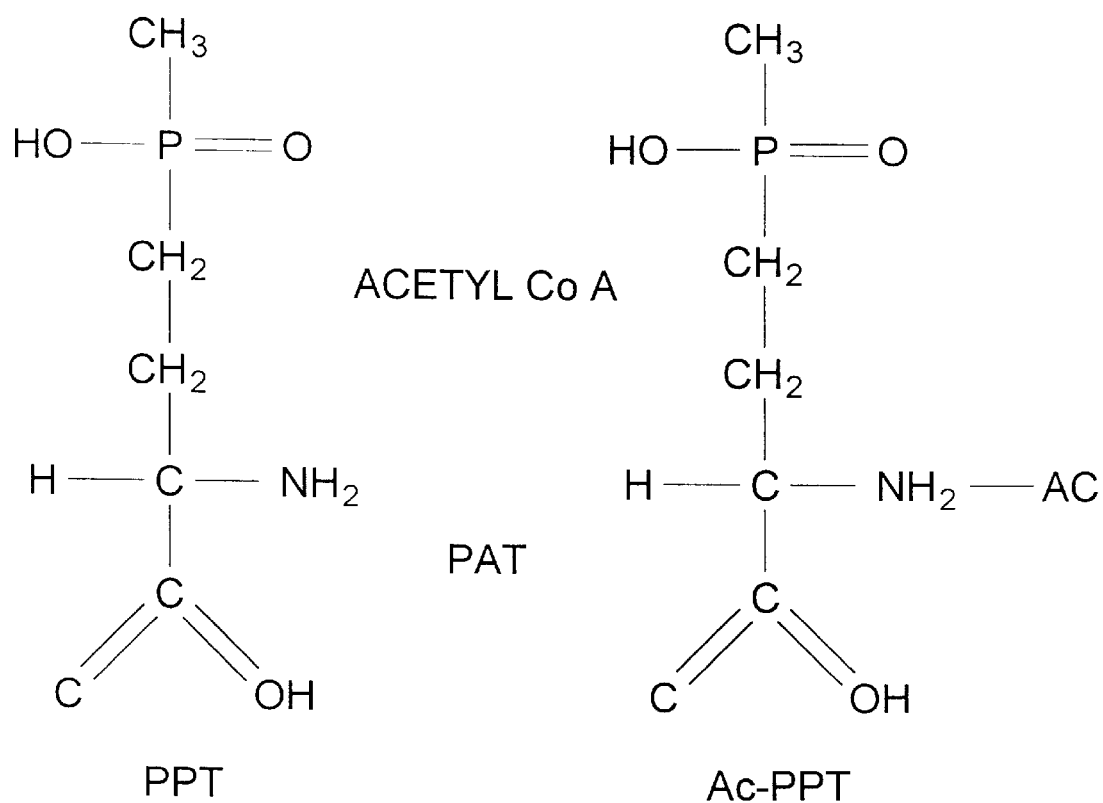

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: synthetic
      oligonucleotide
```

-continued

```
<400> SEQUENCE: 1
tatgaatcag ttccatctac catgagccca gaacga                                36

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tatctgcagt tagatctcgg tgacgggca                                       29
```

NON ANTIBIOTIC SELECTABLE MARKERS FOR LIVE VACCINES

CROSS-REFERENCE TO RELATED APPLICATION

This is a continuation of International Application PCT/GB97/01080, with an international filing date of Apr. 18, 1997, now abandoned.

FIELD OF THE INVENTION

The invention relates to DNA constructs encoding a selectable marker other than an antibiotic resistance marker; vectors and/or cells including said constructs; and vaccines based on said constructs for use in animals and particularly, but not exclusively, for use in humans.

As referred to above antibiotic means any of various chemical substances such as penicillin, ampicillin, streptomycin, neomycin or tetracycline produced by various microorganisms, or their synthetic counterparts.

Description of the Related Art

There is an ongoing need to immunise animals, and in particular humans, against various viruses, bacteria and parasites. The aim of immunisation is typically to elicit a secretory, humoral or cell-mediated immune response to at least one antigen expressed by said virus, bacteria or parasites. To this end, a number of vaccines have been developed, some involving the administration of live oral strains of bacteria such as the live oral salmonella vaccines which are typically based upon strains of salmonella which have been attenuated by the introduction of a non-reverting mutation in a gene(s) in the aromatic biosynthetic pathway, or a stress protein such as HtrA, of the bacteria. Since these oral vaccines were first developed they have been used as carriers for delivering other selected immunogenic antigens and thus serving as what is termed multivalent vaccines i.e. they confer resistance against more than one diseased state. For example, it is known that an attenuated strain of *Salmonella typhi* (Ty21A), which is currently administrated as an oral vaccine against typhoid, can be engineered, typically by chromosomal integration, so as to genetically express at least one antigen from at least one other pathogen. This sort of genetic manipulation does not require the use of a selectable marker. The technique is extremely desirable because the single administration of one vaccine can provide protection against a multitude of diseases.

However, unfortunately, the above multivalent vaccines express recombinant antigen using a single gene copy of the relevant antigen and thus the level of expression is low i.e. less than 1% of total cell protein. For example the expression level of a single copy malarial antigen gene from the chromosome of *Salmonella typhi* has been estimated to be 0.16% of total cell protein (Gonzalez et al 1994). From 10 human volunteers who were vaccinated, in only 3 volunteers were there actually any detectable immune responses (Gonzalez et al 1994). In addition such vaccines may provide for an immune response that is less than desirable, typically in a healthy individual the course of the disease appears unaffected and quantifiable in vitro tests of a routine nature for the same individual are comparably poor.

Thus, contrary to expectations, a multivalent vaccine may in practice only be effective against a single pathogen.

Theoretically, it should be possible to improve the immunogencity of the recombinant antigen by increasing its level of expression. This could be done either by providing for multiple copies of the gene encoding the relevant antigen(s) and/or by genetically engineering the gene so that it is linked to an agent, such as a promoter, providing for high expression. However, in order to assess the success of such genetic engineering it is necessary to include in the engineering process selectable markers so that successfully transformed cells, suitable for use as vaccines, can be identified. Markers that are currently used are antibiotic resistant markers and the tests for successful transformation typically involve exposure of a cell population to a selected antibiotic and subsequent isolation of those cells showing antibiotic resistance.

This extensively used test for determining successful transformation cannot be employed in the manufacture of vaccines for use in either humans or animals. This is because incorporating a gene conferring antibiotic resistance into a vaccine could be potentially hazardous for a number of reasons. Firstly, if an adverse reaction occurred in an unusually suspectable vaccine, the antibiotic could not be administered to the individual to clear the vaccine strain. Secondly it is of concern that the antibiotic resistance gene could be transferred to other microorganisms rendering them no longer amenable to control with the antibiotic.

Thus it can be seen there is a need to provide for multivalent vaccines and in order to achieve this it is necessary to ensure that recombinant genes encoding preselected antigens are expressed to a sufficient level to elicit an immune response. Thus there is a need to use vectors that either comprise multiple copies of the relevant gene and/or at least one copy of the relevant gene operatively linked to a high expression system such as a high expression promoter when transforming a host cell such as an attenuated strain of *Salmonella typhi*. However, to do this, transformation must be assessed using a selectable marker and there is therefore a need to identify a selectable marker that can be used to transform a host cell which, ultimately, will be administered to, or otherwise harboured within, an animal and in particular a human. Thus there is a need to find a safe selectable marker and by this term we mean a marker that can be used in a system, or a cell that will eventually be given to an animal and in particular humans.

DESCRIPTION OF THE INVENTION

It is therefore an object of the invention to provide a multivalent vaccine which is suitable for administration to animals, and particularly but not exclusively, humans.

It is yet a further object of the invention to provide a safe, selectable marker for use, in, or in relation to animal systems.

It is yet a further object of the invention to provide a vector including said safe, selectable marker.

It is yet a further object of the invention to provide a vector including said safe, selectable marker and also at least one gene encoding a selected recombinant antigen which is preferably, but not exclusively, operatively coupled to a high expression promoter.

We have achieved the objects of the invention by identifying a gene that encodes for an agent, other than an antibiotic resistance conferring agent, which is able to counter, or advantageously affect, the otherwise deleterious effect of a given selected substance on a cell to be transformed by a vector including said gene.

In one embodiment of the invention the invention is achieved by use of the BIALAPHOS resistance gene (bar gene).

The gene conferring resistance to BIALAPHOS (the bar gene) was cloned from *Streptomyces hygroscopicus* genomic DNA in 1986 by Murakmi et al.

The bar gene encodes for phosphinothricin acetyltransferase (PAT) which converts the herbicide DL-phosphinothricin (PPT) [CAS No. 77182-82-2 Bellinger R. R., et al Weed Science 33:779 1985], with high affinity, into a non herbicidal acetylated form by transferring the acetyl group from acetyl CoA onto the free amino group of PPT. The reaction mechanism is illustrated in FIG. 1 (Thompson et al).

In the absence of the bar gene PPT is an analogue of glutamate and a specific and very strong inhibitor of glutamine synthetase in both plants and bacteria. Glutamine synthetase plays a central role in the assimilation of ammonia and the regulation of nitrogen metabolism. In fact it is the enzyme that detoxifies ammonia. Thus, in plants, when PPT is applied ammonia metabolism is disturbed and ammonia accumulates to toxic levels in the cells. In bacteria, PPT acts as a bacteriostatic agent as a result of glutamine starvation, in a media lacking this amino acid, as it irreversibly inhibits glutamine synthetase (D'Halluin et al 1992).

As a result of the above described activity of the bar gene product it is possible to use the bar gene as a safe, selectable marker in genetic engineering experiments where it would be otherwise hazardous to use genes encoding substances which can be used by pathogens to obtain resistance to therapeutic agents which are related to said substances, such as antibiotic resistant genes.

In its broadest aspect the invention therefore concerns the use of a safe, selectable marker, i.e. a gene that confers resistance to an agent other than an antibiotic, which agent can be used to deleteriously affect the growth of an organism transformed so as to include at least said marker.

According to a first aspect of the invention there is therefore provided a transformed cell which has been engineered so as to express at least one antigen, homologous or heterologous, and at least one safe, selectable marker which confers on said cell resistance to an agent, other than an antibiotic, which would otherwise deleteriously affect the growth of said cell.

Ideally, expression of said antigen is of a sufficient level to elicit an immune response when said transformed cell is administered to or given to an animal. Thus, multiple copies of the gene encoding said antigen may be provided in said transformed cell and/or at least one copy of said gene is operatively linked to a high expression agent such as a high expression promoter.

In one aspect the invention may involve the genetic manipulation of a bacterial cell so that it expresses at least one antigen, i.e. it is univalent, and in this instance ideally multiple copies of the gene encoding said antigen will be engineered into said cell along with a safe, selectable marker so that successful transformation can be monitored.

Alternatively, said at least one antigen may include a number of different antigens so as to confer on said cell multivalency, and once again, preferably a plurality of copies of the genes encoding the relevant antigens may be provided so as to enhance expression of said antigens. Alternatively or in addition at least one of said antigens is linked to a high expression promoter, and preferably said multiple copies of said antigen; or preferably multiple copies of said multiple antigens maybe linked to a high expression promoter.

Ideally, said promoter is inducible, and preferably inducible in vivo. For example one such promoter is the *E. coli* nitrite reductase promoter, or indeed any other promoter which would favour a high expression of a gene coupled thereto, especially in in vivo conditions.

In any of the above instances successful transformation of said cell is monitored by the safe, selectable marker.

In a preferred embodiment of the invention said cell is of the strain Salmonella such as, for example, *Salmonella typhi*. In this instance the cell is ideally an attenuated strain of *Salmonella typhi*. In addition, in this instance, this cell expresses antigens relating to typhoid fever and the cell is either transformed, less preferably, to express more of said antigens conferring resistance to typhoid fever, or more preferably, to express antigens of a different pathogenic type so as to confer resistance to other pathogens (Khan et al 1994; Chabalgoity et al 1996).

In yet a further preferred embodiment of the invention the said cell includes a construct expressing at least a fragment of tetanus toxoid, and ideally expressing the highly immunogenic but atoxic fragment C (TetC) from tetanus toxin. (Khan et al 1994). However, it is within the scope of the invention for said cell to include any other preferred construct which enhances the immunogenicity of the cell and thus increases the desirability of the use of the cell as a vaccine. One such further example would be the B sub unit of *Vibrio cholerae* or the B sub unit of *Escherichia coli*.

It will be apparent from the above that where said cell, prior to transformation, expresses an antigen, whether homologous or heterologous and thus is univalent, subsequent to transformation, assuming a heterologous antigen is used, then said univalent cell will become multivalent. Moreover, it is possible to increase the valency of the cell by the process of transformation. For example, where said cell expresses either at least one homologous antigen and at least one heterologous antigen, or at least two heterologous antigens, then following the process of transformation, assuming transformation with yet a further heterologous antigen, the valency of the cell will be increased so as to potentially confer resistance against a number of pathogens equal to or less than number of antigen types.

According to a yet further aspect of the invention there is provided a vector comprising at least one gene encoding an agent, other than an antibiotic resistance agent, that counters, or advantageously affects, the otherwise deleterious effects of a substance to which a cell that is to be transformed by said vector is susceptible; and at least one gene encoding a pre-selected antigen.

According to yet a further aspect of the invention there is provided a vector comprising at least one bar gene and at least one gene encoding a pre-selected antigen from at least one pathogen known to cause disease in animals.

Preferably either vector includes multiple copies of said gene encoding said antigen and/or copies of different genes encoding different antigens all selected from pathogens which are capable of causing disease in animals.

More preferably still at least one of the aforementioned genes is operatively coupled to a high expression promoter and ideally at least one of said antigens is coupled to said promoter so as to provide for high expression of at least one of said antigens.

According to a yet further aspect of the invention there is provided a vector including an antibiotic resistance gene into which gene has been inserted a gene encoding resistance to a substance, other than an antibiotic, which substance is capable of deleteriously affecting a cell to be transformed by said vector.

In this aspect of the invention the said antibiotic resistance gene is rendered insertionally inactivated.

In a preferred embodiment of this aspect of the invention the said gene encoding resistance to the substance is the bar gene.

According to yet a further aspect of the invention there is provided a vector including an antibiotic resistance gene into which there has been inserted a gene encoding resistance to a substance, other than an antibiotic, which deleteriously affects the growth of a cell into which said vector is to be inserted; and also at least one gene encoding a selected antigen.

In a preferred embodiment of the invention said selected antigen is heterologous having regard to the nature of the cell to be transformed by said vector.

More preferably further still said vector comprises multiple copies of said antigen and/or at least one, and preferably multiple copies, of at least one other antigen of at least one other pathogen.

Preferably further still at least one of said genes is operatively coupled to a high expression promoter, and ideally, at least one of said genes encoding at least one of said antigens is operatively coupled to said high expression promoter.

According to a yet further aspect of the invention there is provided DNA constructs encoding the characterising parts of the above referred to vectors.

According to a yet further aspect of the invention there is provided a vaccine for use in animals comprising the aforementioned cell and/or vector of the invention.

Suitable antigens for working the invention include, but are not limited to, antigens relating to human immunodeficiency virus (HIV) such as HIV-1 or HIV-2; the CD4 receptor binding site for HIV; hepatitis A or B virus; human rhinovirus such as type 1 or type 14; Herpes simplex virus; poliovirus type 2 or 3; foot-and-mouth disease virus; rabies virus; rotavirus; influenza virus; coxsackie virus; human papilloma virus such as type 16, the E7 protein thereof, and fragments containing the E7 protein; simian immunodeficiency virus; antigens from *Bordetella pertussis* such as the P69 protein and FHA antigens; *Vibrio cholerae; Bacillus anthracis*; and *E.coli* antigens such as LT-B antigens, K88 antigens and enterotoxigenic antigens. Other antigens include the CD4 antigen, *Schistosome mansoni* antigens such as P28 antigens, antigens of flukes, mycoplasma, roundworms, tapeworms, *Chlamydia trachomatis*, and malaria parasites for example parasites of the genus Plasmodium or Babesia. Other antigens include those derived from the mycobacteria.

As mentioned, suitable promoters for use in the invention include promoters which are ideally inducible and so respond to a change in the environment.

An example is a promoter that is inducible having regard to anaerobic conditions such as the nirB promoter.

Suitable cells for working the invention comprise attenuated bacteria such as those selected from the genus Salmonella, Haemophilus, Neisseria, Bordetella, Vibrio or Yersinia, or attenuated mycobacteria. Details of attenuated bacteria are well know to those skilled in the art and will not be described in detail hereinafter.

The vaccine of the invention may comprise at least one suitable adjuvant ideally, the vaccine is provided in a suitable form for oral administration for example in a capsular form in which the vaccine is lyophilised. Alternatively, the lyophilised vaccine may be provided in the form of a suspension suitable for reconstitution prior to administration. Typically reconstitution is provided using suitable buffer to ensure the viability of the organisms. Where the vaccine is to be orally administrated it is desirable to pre-administer an alkaline preparation such as sodium bicarbonate in order to safeguard against the effects of gastric acidity. Alternatively still the vaccine may be supplied in the form of an aerosol.

It will be apparent to those skilled in the art that the dose of the vaccine will be dependant upon a number of variables, not least, the size and weight of the vaccine recipient, the type of vaccine formulated and the immunogenicity of the relevant antigen(s).

An embodiment of the invention will now be described by way of example only with reference to the following figures wherein:

FIG. 1 shows the reaction mechanism catalysed by the bar gene product PAT;

In the following experiments a gene encoding resistance to a substance other than an antibiotic is described and in particular the bar gene encoding resistance to the herbicide PPT. However, it is not intended that the application should be limited by this example rather this example is provided by way of comprehension only.

*Salmonella typhimurium*

Experiments to Show that the Selected Host Cell is Sensitive to PPT

Strains of *E.coli* (TG2) and *S. typhimurium* (CS) were incubated overnight at 37° C. under normal culture conditions and in normal culture medium. Cells from the overnight culture were diluted into phosphate buffered saline (PBS) and a series of serial dilutions plated onto LB plates with PPT at concentrations of 250 ug/ml and 0 ug/ml.

As a result of this incubation we established that in the absence of PPT growth of the two strains proceeded as normal. However growth was totally inhibited at PPT concentrations of 250 ug/ml at dilutions ranging from $10^1$ and $10^5$ of the overnight culture.

This experiment therefore established that our selected host cell was suspectable to PPT.

Experiments to Replace the Antibiotic Resistance Marker of a Salmonella Expression Plasmid with the Bar Gene The plasmid pTETnir15 expresses from the nirB promoter fragment C (TetC) of tetanus toxin (Chatfield et al 1992).

This plasmid contains the gene encoding for beta-lactamase (ampR) which confers resistance to the antibiotic ampicillin. Hence ampicillin resistance is the selectable marker. Ideally we need to introduce the bar gene as a selectable marker, and if possible inactivate the ampR gene. As we do not wish to alter the properties of pTETnir15, which make it a very effective expression system in live vaccines, we wished to incorporate the minimum number of changes in the plasmid.

The ampicillin resistance gene was removed and replaced with the herbicide resistance gene by the following strategy. The 3727 bp pTETnir15 was digested with the restriction enzymes Asp 700 and Pst1 which cut exclusively within the 860 bp ampR gene to release a 354 bp fragment located towards the 5'-end of the gene. The 3373 bp remnant vector was gel-purified and was now ready for cloning in the bar gene.

The plasmid pSCB-1 contains the bar gene and was obtained from PBI Cambridge. A bar gene expression cassette was synthesised by the polymerase chain reaction (PCR; Saiki et al 1988) from pSCB-1.

TATGAATCAGTTCCATCT
ACCATGAGCCCAGAACGA(SEQ ID NO:1)

TATCTGCAGTTAGATCTC GGTGACGGGCA(SEQ ID NO:2)

The reaction was performed using sense and antisense primers designed to amplify the complete open reading frame of the bar gene. In addition to facilitate the cloning of the bar gene the sense primer was tailored with the recognition sequence of the restriction enzyme Asp700 and the antisense primer was tailored with the recognition sequence for Pst1. The product was gel-purified and digested with Asp700 and Pst1, resulting in a bar gene cassette of approximately 579 bp, and then cloned into the residual 3373 bp pTETnir15 plasmid which had also been cut with the respective enzymes. The resulting plasmid was designated pBAT1.

This generated an open reading frame in pBAT1 composed of 59 codons from the ampR gene followed by all the codons from the bar gene cassette terminating in a stop codon, followed by the remaining 92 codons from the ampR gene. This results in the expression of a short 59 amino acid N-terminal fusion of AmpR to the full length Bar. This approach has the advantage that it allows the expression of the bar gene by the natural ampR promoter, retains the integrity of the ribosome binding sequence, and allows the bar gene to utilise the signal sequence of ampR. Furthermore, this strategy allows the ampR gene to be partially deleted and insertionally inactivated.

Experiments to Test the Ability of the Bar Gene in PBATI to Confer Resistance to PPT in Salmonella The construct was electroprated into electrocompetent C5htrA cells and transformants selected by adding cells to molten (48° C.) minimal agar supplemented with M9 salts. Transformed C5htrA cells harbouring pBAT1 were selected by the addition of PPT (250 ug/ml) and 100 ul droplets spotted onto a petridish. The plates were then incubated at 37° C. for 48 hours.

The agar droplets were then transferred to minimal broth media supplemented with M9 salts containing 375 ug/ml of PPT. The cells were grown shaking at 37° C. overnight. A stock of the culture was made prior to harvesting the cells and purifying the pBAT1 plasmid DNA. The identity of the construct was verified by restriction enzyme mapping with EcoR1 and Pst1.

Furthermore pBAT1 (C5htrA) is inhibited from growth in media supplemented with ampicillin (50 ug/ml), suggesting there is no remaining residual activity from the partially deleted and insertionally disrupted ampR gene as expected.

In summary pBAT1 has been constructed. This plasmid expresses the bar gene and is capable of conferring PPT resistance to the host *S. typhimurium* C5htrA vaccine strain allowing this herbicide to be used as a selective marker for cells harbouring this construct.

Experiments to Show that the Bar Gene does not Alter the Physiology of the Host Salmonella For the bar gene to be a selective marker of practical value in a vaccine, host vaccine cells harbouring the constructs containing the marker should retain their original properties. For example the plasmid should be able to continue to express guest antigens, and remain stable by not being segregated and lost from the host cell population in the absence of marker selection.

The ability of pBAT1 (C5htrA) to express TetC was compared to pTETnir15 (C5HtrA) by SDS-PAGE and immunoblotting of these cells. In each case probing the immunoblots with a rabbit anti TetC polyclonal sera revealed no difference in the expression levels and stability of the 50 kDa TetC band.

Thus it can be concluded that there is no aberrant expression of TetC from the pBAT1 construct.

The ability of pBAT1 to be stably retained in C5HtrA in the absence of marker selection was investigated and compared to pTETnir15 in C5HtrA.

The strains were grown in the liquid media already described above supplemented with either PPT (375 ug/ml) or ampicillin (50 ug/ml) shaking overnight at 37° C. The following day the cultures were diluted 1 in a 100 into fresh media, each with and without the respective selective marker. The four cultures were again shaken at 37° C. and the following culture dilutions ranging $10^6$ to $10^8$ plated out onto minimal agar plates, again with and without the selective marker for each of the four cultures.

The number of colonies arising from each of the four cultures plated on minimal media with and without selection was determined. For pBAT1 (C5HtrA) and pTETnir15 (C5HtrA) the number of colonies counted from liquid cultures which had been grown in the presence and absence of selection yielded the same number of colonies on plates with/without the selective marker. This would strongly suggest the plasmid pBAT1 is as stably inherited as pTETnir15 in the absence of selection with either PPt or ampicillin respectively.

Thus it can be concluded that the bar gene product does not place the host cells harbouring the construct at a selective disadvantage. This implies that the expression of the bar gene does not significantly alter the physiology of the host cell and this of course is a highly desirable property.

*Salmonella typhi*

Experiments to Show that *Salmonella typhi* is Sensitive to PPT

To investigate the possibility that *S.typhi* is sensitive to the bacteriocidal effects of PPT, the following experiment was conducted. The *S.typhi* stain 541Ty [Edwards and Stocker, 1981] was selected as a model strain. 541Ty has a number of nutritional requirements and was therefore grown in minimal media with M9 salts and the following supplements. To 5 ml of media 25 ul of each of the following were added: 1% L-serine, 1% pyridoxine, 0.1% 2,3-dihydroxybenzoic acid (DHB), 1% L-histidine, 1% L-adenine, 1% cystine, 1% L-tryptophan, and Aro mix (1% L-phenylalanine, 1% L-tyrosine, 1% L-tryptophan, 0.1% para-aminobenzoic acid (PABA), 0.1% DHB).

The strain 541Ty was incubated overnight at 37° C. under normal culture conditions in minimal media with the 541Ty supplements described above either alone, and also with PPT at 350 ug/ml. After the incubation it was observed that the culture supplemented with PPT, in contrast to the culture lacking PPT, had failed to grow.

This experiment therefore established that our selected *S.typhi* host strain is indeed susceptible to the bacteriocidal effects of PPT.

REFS:

Construction of ΔaroA his Δpur strians of *Salmonella typhi*. Edwards F., Stocker B.
Journal of Bacteriology 170: 3991–3995, 1988.

Experiments to Test the Ability of the Bar Gene in pBAT1 to Confer Resistance to PPT in *Salmonella typhi*

The construct pBAT1 was electroplated into electrocompetent 541Ty cells and transfornants selected by adding cells to molten (48° C.) minimal agar with the supplements already described above, and also PPT (350 ug/ml) to select for transformants. The plates were then incubated at 37° C. for 48 hours.

The recombinant clones were picked and grown shaking for 36 hours in minimal media with the 541Ty supplements already described, and PPT (350 ug/ml). Stocks of the clones were made prior to inoculating the cultures. Cells were harvested and the plasmid pBAT1 isolated. The identity of the construct was verified by restriction enzyme mapping with Eco R1 and Pstl.

In summary, the plasmid pBAT1 expresses the bar gene and is capable of conferring PPT resistance to the host S.typhi strain, allowing this herbicide to be used as a selective marker for S.typhi cells harbouring this construct.

Experiments to Show that the Bar Gene does not Alter the Physiology of the Host Salmonella typhi For the bar gene to be a selective marker of practical value in a vaccine, host vaccine cells harbouring the constructs containing the marker should retain their original properties. For example the plasmnid should be able to continue to express guest antigens, and remain stable by not being segregated and lost from the host cell population in the absence of marker selection.

The ability of pBAT 1(541Ty) to express TetC was compared to pTETnir15(541Ty) by SDS-PAGE and immunoblotting of these cells. In each case probing the immunblots with a rabbit anit TetC polyclonal sera revealed no difference in the expression levels and stability of the 50 kDa TetC band.

Thus it can be concluded that there is no aberrant expression of TetC from the pBAT1 construct.

The ability of pBAT1 to be stably retained in 541Ty in the absence of marker selection was investigated and compared to pTETnir15 in 541Ty.

The strains were grown in the liquid media already described above supplemented with either PPT (375 ug/ml) or ampicillin (50 ug/ml) shaking overnight at 37° C. The following day the cultures were diluted 1 in a 100 into fresh media, each with and without the respective selective marker. The four cultures were again shaken at 37° C. and the following culture dilutions ranging $10^6$ to $10^8$ plated out onto minimal agar plates with the 541Ty supplements, again with and without the selective marker for each of the four cultures.

The number of colonies arising from each of the four cultures plated on 541Ty minimal media with and without selection was determined. For pBAT1 (541Ty) and pTETnir15 (541Ty) the number of colonies counted from liquid cultures which had been grown in the presence and absence of selection yielded the same number of colonies on plates with/without the selective marker. This would strongly suggest the plasmid pBAT1 is as stably inherited as pTETnir15 in the absence of selection with either PPT or amnpicillin respectively.

Thus it can be concluded that the bar gene product does not place the host *S.typhi* cells harbouring the construct at a selective disadvantage. This implies that the expression of the bar gene does not significantly alter the physiology of the host *S.typhi* and this of course is a highly desirable property.

SUMMARY

We have therefore shown that it is possible to produce a vaccine for use in animals, and in particular for use in humans, which maybe either univalent or multivalent, but in any event, comprises a transformed host cell wherein successful transformation is determined having regard to the resistance of the host cell to a pre-selected substance by virtue of the transformation of the said host cell with a gene conferring resistance to said substance, other than an antibiotic resistance gene.

REFERENCES

Gonzalez C., Hone D., Noriega F. R., Tacket C. O., Davis J. R., Losonsky G., Nataro J. P., Hoffman S., Malik A., Nardin E., Sztein B., Heppner D. G., Fouts T. R., Isibasi A., L-evine M. M. Journal of Infectious Diseases 169: 927–31, 1994.

Murakami T., Anzai H., Imai S., Satoh H., Nagaoka K., Thompson C. J. Molecular and General Genetics, 205: 42–50, 1986.

Thompson C. J., Morva N. R., Tizard R., Crameri R., Davis J. E., Lauwereys M., Botterman J. EMBO Journal, 6: 2519–2523, 1987.

Khan C. M. A., Villarreal-Ramos B., Pierce R. J., Riveau G., Demarco de Hormaeche, McNeill H., Ali T., Fairweather N., Chatfield S., Capron A., Dougan G., Hormaeche C. E. Proceedings of the National Academy of Sciences, USA. 91: 11261–11265, November 1994.

Chabalgoity J. A., Khan C. M. A., Nash A. A., Horrnaehe C. E. Molecular Microbiology 19: 791–801, 1996.

Chatfield S. N., Charles I. G., Makoff A. J., Oxer M. D., Dougan G., Slater D., Fairweather N. F., Bio/Technology 10: 888–892, 1992.

Saiki R. K., Gelfand D. H., Stoffel S., Scharf S. J., Higuchi R., Horn G. T., Mullis K. B., Ehrlich H. A. Science 239: 487–491, 1988.

D'Halluin K., De Block M., Denecke J., Janssens J., Leemans J., Reynaerts A., Botterman J., Methods in Enzymology 216: 415–426, 1992.

What is claimed is:

1. A transformed cell which has been engineered so as to express at least one antigen and at least one safe, selectable marker which confers on said cell resistance to an agent, other than an antibiotic, which would otherwise deleteriously affect the growth of said cell, wherein said cell is an attenuated strain of its natural counterpart.

2. A transformed cell according to claim 1 wherein said cell has been engineered to express a plurality of antigens.

3. A transformed cell according to claim 1 wherein multiple copies of the gene encoding said at least one antigen are provided.

4. A transformed cell according to claim 1 wherein said at least one antigen is operatively linked to a high expression promoter.

5. A transformed cell according to claim 4 wherein said promoter is inducible.

6. A transformed cell according to claim 5 wherein said promoter is inducible in vivo.

7. A transformed cell according to claim 1 wherein said cell is adapted to express at least a fragment of tetanus toxoid.

8. A transformed cell according to claim 7 wherein said fragment is the highly immunogenic but atoxic fragment C (TetC) from tetanus toxin.

9. A transformed cell according to claim 1 wherein said cell is engineered to express an agent that enhances the immunogenicity of the cell.

10. A transformed cell according to claim 1 wherein said safe, selectable marker is a product of the bar gene.

11. A vector comprising at least one gene encoding an agent, other than an antibiotic resistance agent, that counters, or advantageously affects, the otherwise deleterious effects of a substance to which a cell that is to be transformed by said vector is susceptible; and at least one gene encoding an antigen from at least one pathogen known to cause disease in animals.

12. A vector according to claim 11 wherein said vector comprises at least one copy of the bar gene.

13. A vector according to claim 11 wherein said vector includes multiple copies of said gene encoding said antigen.

14. A vector according to claim 11 wherein said vector includes genes encoding a plurality of different antigens all selected from pathogens which are capable of causing disease in animals.

15. A vector according to claim 11 wherein said at least one gene encoding said antigen is operatively linked to a high expression promoter.

16. A vector according to claim 15 wherein said promoter is inducible.

17. A vector according to claim 16 wherein said promoter is inducible in vivo.

18. A vector according to claim 11 wherein said vector includes an antibiotic resistance gene which is made insertionally inactive by the insertion therein of at least one gene encoding a product that, directly or indirectly, confers resistance to a substance, other than an antibiotic, which substance is capable of deleteriously affecting a cell to be transformed by said vector.

19. A vector according to claim 18 wherein said gene encoding resistance to said substance is the bar gene.

20. A vector according to claim 18 wherein, optionally or additionally, a gene encoding at least one antigen is inserted into said antibiotic resistance gene so as to render said gene insertionally inactive.

21. A transformed cell according to claim 1 wherein the cell is a Salmonella cell.

22. A transformed cell according to claim 21 wherein the cell is a *Salmonella typhi* cell.

* * * * *